United States Patent [19]

Keckler et al.

[11] Patent Number: 5,959,134

[45] Date of Patent: Sep. 28, 1999

[54] RECOVERY OF ORGANICS FROM PROCESS FLARE HEADER

[75] Inventors: Kenneth P. Keckler, Lima; Sanjay P. Godbole, Solon, both of Ohio

[73] Assignee: The Standard Oil Company, Chicago, Ill.

[21] Appl. No.: 09/082,403

[22] Filed: May 20, 1998

[51] Int. Cl.⁶ .................................................. C07C 253/00

[52] U.S. Cl. .............................................................. 558/320

[58] Field of Search ............................................... 558/320

[56] References Cited

FOREIGN PATENT DOCUMENTS 59-080650   5/1984   Japan .
60-147288   8/1985   Japan .

Primary Examiner—Johann Richter
Assistant Examiner—Joseph Murray
Attorney, Agent, or Firm—Joseph DiSalvo; Stephen L. Hensley

[57] ABSTRACT

A process for the enhanced recovery of waste organics, mainly hydrogen cyanide (HCN) and acrylonitrile, from the process flare material obtained from the reactor effluent of an ammoxidation reaction of propylene or isobutylene.

8 Claims, No Drawings

5,959,134

RECOVERY OF ORGANICS FROM PROCESS FLARE HEADER

FIELD OF THE INVENTION

The present invention is directed to an improved process for the manufacture of acrylonitrile or methacrylonitrile. In particular, the present invention is directed to the improvement in the recovery of hydrogen cyanide utilized during the manufacture of acrylonitrile or methacrylonitrile.

Recovery of byproduct hydrocyanic acid (HCN) produced when acrylonitrile/methacrylonitrile is manufactured by the ammoxidation of propylene or isobutylene on a commercial scale has been accomplished by quenching the reactor effluent with water followed by passing the gaseous stream (containing acrylonitrile or methacrylonitrile, as well as byproduct HCN) resulting from the quench to an absorber where water and the gases are contacted in counter-current flow to remove substantially all the HCN and acrylonitrile or methacrylonitrile. The aqueous stream containing HCN and the acrylonitrile or methacrylonitrile is then passed through a series of distillation columns and associated decanters for separation and purification of product acrylonitrile or methacrylonitrile from a vapor stream containing substantially all the HCN.

Typical recovery and purification systems that are used during the manufacture of acrylonitrile or methacrylonitrile are disclosed in U.S. Pat. Nos. 4,234,510 and 3,885,928, assigned to the assignee of the present invention and herein incorporated by reference.

SUMMARY OF THE INVENTION

It is the primary object of the present invention to provide an improved process for the recovery of byproduct HCN in the manufacture of acrylonitrile or methacrylonitrile.

It is a further object of the present invention to provide an improved process for the manufacture of acrylonitrile or methacrylonitrile which reduces the amount of acrylonitrile and HCN directed to incineration or other recovery processes.

It is yet a further object of the present invention to provide an improved method for the recovery of organic material obtained in the reactor effluent of an ammoxidation reaction of propylene or isobutylene for the production of acrylonitrile or methacrylonitrile, by directing at least a portion of the process flare header material to an organic recovery process.

An additional object of the present invention is the use of aqueous phase countercurrent scrubbing, organic phase countercurrent scrubbing, aqueous phase co-current scrubbing, organic phase co-current scrubbing, distillation, extraction, leaching, adsorption, absorption, selective condensation, and selective reaction to effect the recovery of organic material obtained in the reactor effluent of an ammoxidation reaction of propylene or isobutylene for the production of acrylonitrile or methacrylonitrile.

Another object of the current invention is to provide a process for the manufacture of acrylonitrile or methacrylonitrile, comprising transporting a portion of process flare header contents obtained during the ammoxidation of propylene or isobutylene to a contacter where the process flare header contents are contacted with an aqueous stream and at least a portion of organic materials contained in the flare header contents are absorbed in the aqueous stream.

An additional object of the present invention is the use of one or more countercurrent scrubbers, co-current scrubbers, distillation columns, extraction columns, leaching columns, adsorption towers, absorption towers, or selective condensation towers to effect an improved process for the manufacture of acrylonitrile or methacrylonitrile.

Additional objects, advantages and novel features of the invention will be set forth in part in the description which follows, and in part, will become apparent to those skilled in the art upon examination of the following or may be learned by the practice of the invention. The objects and advantages of the invention may be realized and obtained by means of the instrumentalities and combinations particularly pointed out in the appended claims. To achieve the foregoing and other objects and in accordance with the purpose of the present invention as embodied and broadly described herein, the process of the present invention comprises transporting the reactor effluent obtained during the ammoxidation of propylene or isobutylene to a quench column wherein the hot effluent gases are cooled by contact with an aqueous spray, passing the cooled reactor effluent overhead to an absorber column wherein the HCN and crude acrylonitrile or methacrylonitrile is absorbed in water, passing the aqueous solution containing the HCN and acrylonitrile or methacrylonitrile, plus other impurities to a first distillation column (recovery column), where a significant portion of the water and impurities are removed as a liquid bottoms product, while HCN, water, a minor portion of impurities and acrylonitrile or methacrylonitrile are removed as an overhead vapor stream. Throughout the process, various vapor streams from the process units are vented to a process flare header, which directs these materials to a high temperature thermal oxidizer, or flare, for safe and efficient disposal.

The current invention improves the past operation by adding an additional HCN recovery unit to the process flare header.

In a preferred embodiment of the present invention, the recovery process is performed by directing the contents of the process flare header to a counter-current two phase contactor, wherein the gaseous contents of the process flare header are directed upwards in a process vessel, and an aqueous stream flowing downwards contacts the gaseous process flare header materials to extract the HCN therein.

The present invention allows for the more effective recovery of HCN. This improved recovery means that less HCN is directed to incineration, with the resulting decrease in emissions from waste gas combustion.

DETAILED DESCRIPTION OF THE INVENTION

The general recovery and purification of acrylonitrile of methacrylonitrile, and the present invention will now be described. The reactor effluent obtained by the ammoxidation of propylene or isobutylene, ammonia and oxygen containing gas in a fluid bed reactor while in contact with a fluid bed ammoxidation catalyst is transported to a quench column via a transfer line, wherein the hot effluent gases are cooled by contact with water spray. The cooled effluent gas containing the desired product (acrylonitrile or methacrylonitrile, acetonitrile and HCN) is then passed into the bottom of an absorber column via a transfer line wherein the products are absorbed in water which enters absorber column from the top. The non-absorbed gases pass from the absorber through a pipe located at the top of the absorber and may be directed to the process flare header, or to further recovery processes. The aqueous stream containing the desired product is then passed via a bottoms line from the bottom of absorber to the upper portion of a first distillation column (recovery column) for further product purification. The product is recovered as a liquid from the top portion of recovery column and sent to a second distillation column (heads column) via a feed line, while water and other impurities are removed from the recovery column bottom. Non-condensable gases present at the top of the recovery column may also be directed to the process flare header. In the heads column, the HCN is taken overhead and removed from the column, cooled in an overhead condenser, and the resulting material directed to reflux drum. Liquid reflux from the reflux drum is returned to the upper portion of the heads tower. Vapor phase material is also removed from the reflux drum and cooled in an HCN product condenser. The cooled and partially condensed effluent of the HCN product condenser is directed to the HCN knock-out pot. The liquid portion of the HCN is removed from the HCN knock-out pot and returned to the recovery process. Uncondensed HCN, along with other noncondensable material, is removed from the HCN knock-out pot, and may be sent via the process flare header directly to an incinerator, or purified and recovered by conventional means known in the art. There are other process streams also sent to the process flare header for safe disposal.

A significant operational problem experienced in the recovery and purification of products in the acrylonitrile and methacrylonitrile production process is the formation of polymeric HCN, primarily in the quench and heads column. In particular, polymeric HCN forms on the trays and internals in the heads column above the column feed location. The solid, polymeric HCN fouls distillation trays, over flow weirs, downcomers, and the like, as well as disrupting the hydraulic balance of the liquid/vapor interfaces in the heads column.

The formation of polymeric HCN is well known, but not well understood or quantified. When process units, particularly the heads column, are inspected and cleaned during routine maintenance, the polymeric HCN is removed from the process, along with any accumulation of corrosion byproducts and debris. Historically, the quantity of polymeric HCN has not been measured accurately, but rather have been qualitatively assessed for it's impact on process operability.

Additionally, extremely accurate measurement of the amount of HCN in the process flare material is very difficult. Because large quantities of non-condensable gases, such as nitrogen and light hydrocarbons, are vented to the process flare header, any minute sampling error is magnified when HCN content is calculated. Such sampling error can occur as a result of slight imbalances in isokinetic sampling procedures, slight calibration errors in compositional determination techniques, and sample degradation. An even more significant disparity can occur due to the dynamic nature of the manufacturing and recovery process. The units that direct material to the process flare header operate over a range of conditions, and every perturbation of one process unit affects the operation of all process units that receive heat or material from the perturbed unit. Thus, any sampling must be based upon a clear understanding of the process operation, and also upon assumptions of which parameter best describe typical operation.

As a result of an imperfect understanding of the process chemistry and process flare header material composition, operators of acrylonitrile and methacrylonitrile production facilities attributed most losses of HCN to the formation of polymeric HCN when performing material balances around their facilities. Common belief, based upon many years of plant data, was that less than one percent (1%) of byproduct HCN produced in such facilities was directed to the process flare header. Although the loss of this material was an economic loss, the dilute concentration of HCN in the process flare header material did not justify the extreme measures needed to recover the material. This valuable byproduct was burned in the process flare for safety reasons, because the costs of recovery were believed to be too high.

In an effort to further reduce any environmental impact resulting from incinerating the HCN in the process flare, an additional countercurrent scrubber was installed to process the contents of the process flare header. The contents of the process flare header were contacted with an aqueous liquid stream flowing in the opposite direction. The non-condensible portions of the process flare header material disengaged from the aqueous stream, and was directed to the process flare header and burned, as before. The aqueous liquid stream was returned to the recovery and purification process, and commingled with the large aqueous stream which is used for absorbing desired products exiting the reactor and subsequently distilled to the desired purity level.

Upon evaluating the composition of the aqueous liquid stream returned to the recovery process from the process flare header scrubber, it was discovered that almost ten percent (10%) of the theoretical yield of byproduct HCN had been recovered, almost an order of magnitude greater than the amount of HCN believed to exist in the process flare header material. The high level of HCN in the process flare header material was totally unexpected to operators of such facilities. Until the material was actually recovered, those skilled in the art of manufacturing and purifying acrylonitrile or methacrylonitrile had no appreciation for the high levels of valuable HCN byproducts which had been directed to the process flare over years of operation, nor the economic benefits which could have been realized by recovering the HCN at those levels.

Compared to measurement of HCN in the vapor phase material in the process flare header, recovery by countercurrent aqueous scrubbing yields many times the amount of recovered HCN expected. The difficulty of accurate vapor phase HCN measurement, coupled with the belief that a significantly greater amount of HCN was polymerizing in the process equipment and the difficulty in quantifying the actual amount of polymeric HCN recovered during maintenance procedures, led practitioners skilled in the art to conclude that only small quantities of HCN would be available for recovery from the process flare material. Only the actual implementation of a recovery process provided an indication of the true magnitude of the previous amount of HCN burned in the process flare.

Although a countercurrent aqueous contactor was used to recover HCN from the process flare header material, other processes well know in the art could also be used with similar results. Such processes include, but are not limited to, aqueous and organic phase countercurrent and co-current scrubbers, distillation, extraction, leaching, adsorption, absorption, selective condensation, selective reaction, and the like. There is an additional constraint of low pressure drop for the operation of the flare header system without resulting in higher back pressure. Additional concerns relate to maintaining the integrity of flare system as an emergency relief and control system when installing a system to scrub or capture additional materials from the normal vent streams.

Preferably, the ammoxidation reaction is performed in a fluid bed reactor although other types of reactors such as transport line reactors are envisioned. Fluid bed reactors, for the manufacture of acrylonitrile are well known in the prior art. For example, the reactor design set forth in U.S. Pat. No. 3,230,246, herein incorporated by reference, is suitable.

Conditions for the ammoxidation reaction to occur are also well known in the prior art as evidenced by U.S. Pat. Nos. 5,093,299; 4,863,891; 4,767,878 and 4,503,001; herein incorporated by reference. Typically, the ammoxidation process is performed by contacting propylene or isobutylene in the presence of ammonia and oxygen with a fluid bed catalyst at an elevated temperature to produce the acrylonitrile or methacrylonitrile. Any source of oxygen may be employed. For economic reasons, however, it is preferred to use air. The typical molar ratio of the oxygen to olefin in the feed should range from 0.5:1 to 4:1, preferably from 1:1 to 3:1. The molar ratio of ammonia to olefin in the feed in the reaction may vary from between 0.5:1 to 5:1. There is really no upper limit for the ammonia-olefin ratio, but there is generally no reason to exceed a ratio of 5:1 for economic reasons.

The reaction is carried out at a temperature of between the ranges of about 260° to 600° C., but the preferred ranges being 310° to 500° C., especially preferred being 350° to 480° C. The contact time, although not critical, is generally in the range of 0.1 to 50 seconds, with preference being to a contact time of 1 to 15 seconds.

In addition to the catalyst of U.S. Pat. No. 3,642,930, other catalysts suitable for the practice of the present invention are set forth in U.S. Pat. No. 5,093,299, herein incorporated by reference.

As will be evident to those skilled in the art, various modifications of this invention can be made or followed in light of the foregoing disclosure and discussion without departing from the spirit and scope of the disclosure or from the scope of the claims.

What is claimed is:

1. A method of improved recovery of the reactor effluent of an ammoxidation reaction of propylene or isobutylene for the production of acrylonitrile or methacrylonitrile, comprising directing at least a portion of the process flare header material to an organic recovery process selected from the group consisting of aqueous phase countercurrent scrubbing, organic phase countercurrent scrubbing, aqueous phase co-current scrubbing, organic phase co-current scrubbing, distillation, extraction, leaching, adsorption, absorption, selective condensation, and selective reaction.

2. The method of claim 1, wherein said organic recovery process comprises aqueous phase countercurrent scrubbing.

3. The method of claim 1, wherein said organic recovery process comprises aqueous phase co-current scrubbing.

4. A process for the manufacture of acrylonitrile or methacrylonitrile comprising transporting a portion of process flare header contents obtained during the ammoxidation of propylene or isobutylene to a contacter wherein said process flare header contents are contacted with an aqueous stream, wherein at least a portion of organic materials contained in said flare header contents are absorbed in said aqueous stream.

5. The process of claim 4, wherein said contacter is selected from the group consisting of countercurrent scrubber, co-current scrubber, distillation column, extraction column, leaching column, adsorption tower, absorption tower, and selective condensation tower.

6. The process of claim 5 wherein said contacter is a countercurrent scrubber.

7. The process of claim 5 wherein said contacter is a co-current scrubber.

8. The process of claim 5 wherein said contacter is a distillation column.

* * * * *